United States Patent [19]

Hof et al.

[11] Patent Number: 5,260,321
[45] Date of Patent: Nov. 9, 1993

[54] USE OF 1,4-DIHYDROPYRIDINE DERIVATIVES AND COMBINATIONS THEREOF WITH CALCITONINS

[75] Inventors: Robert P. Hof, Gelterkinden; Moise Azria, Basel, both of Switzerland

[73] Assignee: Sandoz Ltd., Basel, Switzerland

[21] Appl. No.: 728,911

[22] Filed: Jul. 12, 1991

Related U.S. Application Data

[63] Continuation of Ser. No. 469,851, Jan. 10, 1990, abandoned, which is a continuation of Ser. No. 120,566, Oct. 29, 1987, abandoned, which is a continuation of Ser. No. 885,625, Jul. 8, 1986, abandoned.

[30] Foreign Application Priority Data

Nov. 12, 1984 [GB] United Kingdom ............... 8428552

[51] Int. Cl.$^5$ ................. C07D 413/04; C07D 417/04
[52] U.S. Cl. ................................ 514/338; 546/271
[58] Field of Search .................... 546/271; 514/338

[56] References Cited

U.S. PATENT DOCUMENTS

| | | | |
|---|---|---|---|
| 4,442,112 | 4/1984 | Müller-Schweinitzer | 544/80 |
| 4,466,972 | 8/1984 | Neumann | 544/80 |
| 4,607,041 | 8/1986 | Baxter et al. | 514/318 |

FOREIGN PATENT DOCUMENTS

| | | |
|---|---|---|
| 0000150 | 1/1979 | European Pat. Off. |
| 0117888 | 9/1984 | European Pat. Off. |
| 3222367 | 12/1983 | Fed. Rep. of Germany |
| 2528431 | 12/1983 | France |
| 2037766 | 7/1980 | United Kingdom |
| 2041358 | 9/1980 | United Kingdom |

OTHER PUBLICATIONS

Current Therapeutics, vol. 24, No. 12, pp. 13–23 (1983).
Drugs of the Future, vol. 8, No. 2, pp. 136 & 137 (1983).
Habib et al. Circ. Res. 58: 305–309, 1986.
Van Valen et al. Fed. Proc. 44 (3), 1985, No. 1909.
Day et al. Lab. Animal Science vol. 27, No. 5, pp. 817–821, 1977.
Family Medical Guide Cooley, pp. 122–124, 1980.
The World Book Illustrated Home Medical Encyclopedia, vol. one, p. 81, 1961.

*Primary Examiner*—Jane T. Fan
*Attorney, Agent, or Firm*—Robert S. Honor; Melvyn M. Kassenoff; Joseph J. Borovian

[57] ABSTRACT

Use of calcium antagonists of formula I

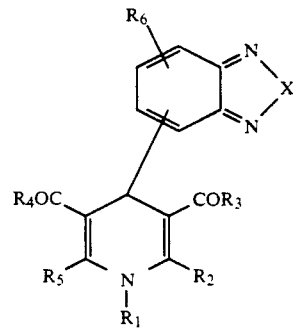

wherein the substituents have various significances in the treatment of conditions related directly or indirectly to ionized calcium levels in the blood and combinations of calcium antagonists, e.g. of formula I, with calcitonins.

6 Claims, No Drawings

USE OF 1,4-DIHYDROPYRIDINE DERIVATIVES AND COMBINATIONS THEREOF WITH CALCITONINS

This is a continuation of application Ser. No. 07/469,851, filed Jan. 10, 1990, which in turn is a continuation of application Ser. No. 07/120,566, filed Oct. 29, 1987, which in turn is a continuation of application Ser. No. 06/885,625, filed Jul. 8, 1986, all of which are now abandoned.

This invention relates to calcium antagonists. Such compounds are also called calcium entry blockers. Calcium antagonists represent a group of active substances which modulate entry of Ca (2+) ions through specific Ca (2+) channels in smooth muscle and are useful for the treatment of inter alia Angina pectoris, hypertension and for some products also migraine.

One group of calcium antagonists are characterised by a 1,4-dihydropyridine structure having an aryl or heterocyclic group attached to the 4 position.

In one aspect the invention relates to a new use of a compound of formula I

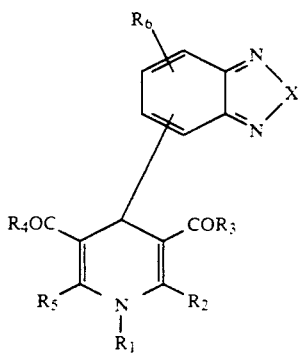

wherein
- $R_1$ is hydrogen, alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, phenylalkyl of 7 to 9 carbon atoms or phenylalkenyl of 9 to 12 carbon atoms, the phenyl ring being unsubstituted or mono-, di- or trisubstituted independently by halogen, hydroxy or alkyl or alkoxy of 1 to 4 carbon atoms,
- $R_2$ and $R_5$, independently, are hydrogen or alkyl of 1 to 6 carbon atoms,
- $R_3$ and $R_4$, independently, are alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, alkoxy of 1 to 6 carbon atoms, hydroxyalkoxy of 2 to 6 carbon atoms, alkoxyalkoxy of 3 to 6 carbon atoms, hydroxyalkoxyalkoxy of 4 to 8 carbon atoms, alkenyloxy or alkinyloxy of 3 to 6 carbon atoms, cycloalkyloxy of 3 to 7 carbon atoms or cycloalkylalkoxy of 4 to 8 carbon atoms,
- $R_6$ is hydrogen, halogen, alkyl or alkoxy or alkylthio or alkylsulfonyl, each of 1 to 4 carbon atoms, trifluoromethyl, nitro or hydroxy, and
- X is oxygen or sulphur.

Certain pharmacological activities of the compounds of formula I have been published in e.g. European Patent specification No. 150.

Particularly interesting compounds of this group of compounds include PY 108-068, i.e. darodipine, i.e. 4-(2,1,3-benzoxadiazol-4-yl)-1,4-dihydro-2,6-dimethylpyridine-3,5-dicarboxylic acid diethyl ester, herein-after referred to as PY; PN 200-110 i.e. 4-(2,1,3-benzoxadiazol-4-yl)-1,4-dihydro-2,6-dimethyl-3-methoxycarbonyl-pyridine-5-carboxylic acid isopropyl ester, hereinafter referred to as PN; and PK 107-959, i.e. 4-(2,1,3-benzothiadiazol-4-yl)-2,6-dimethyl-1,4-dihydropyridin-3,5-dicarbocylic acid dimethylester, hereinafter referred to as PK.

Calcium antagonists, e.g. a compound of formula I, modulate calcium ion transport systems at the cellular level and this has been extensively published in the literature. Movements at the cellular level are, however, very low and changes in the total levels of calcium ions in the blood would not be expected.

We have now found that ionized calcium levels in the blood are lowered to a significant extent by a compound of formula I over a long period of time. These compounds are therefore useful in the treatment of conditions related directly or indirectly to ionized calcium levels in the blood, particularly abnormal or elevated calcium levels in the blood, especially
hypercalcaemic disorders
Morbus Paget
osteoporosis
arteriosclerosis and in particular atherosclerosis (prevention or inhibition of plaque formation)
algoneurodystrophy and
acute pancreatitis.

The present invention in one aspect provides a method of treating a subject suffering from a condition related directly or indirectly to ionized calcium levels in the blood, in particular from a hypercalcemic disorder, Morbus Paget, osteoporosis, arteriosclerosis, algoneurodystrophy or acute pancreatitis, which comprises administering a compound of formula I to the subject. In another aspect the present invention provides a method of reducing ionized calcium levels in a subject which comprises administering a compound of formula I to a subject in need of such treatment.

The compound of formula I preferably is PY, PK or especially PN.

The effect of the compounds of the invention in lowering calcium levels is indicated in any standard animal test for hypercalcemic activity. In one test the compound is administered to rabbits (e.g. ca. 1 kg in weight) either as a suspension e.g. 0.1 to 5 mg (e.g. 0, 1 mg) per ml of solution (i.e. blood plasma with ca. 1-5% alcohol) and 0.1-5 mg/kg animal body weight by intravenous infusion (0.5 ml per hour) or orally e.g. 1 to 5 mg/kg animal body weight as a suspension in distilled water. A significant lowering of calcium ions is observed using standard measuring techniques for calcium ions in the blood, e.g. using a calcium ion selective electrode, or by photometric methods.

One method for measuring calcium ion concentrations is as follows:

The test involves continuous measurement of the ionized calcium concentration in the blood of young rabbits by means of a flow-through system containing $Ca^{2+}$-selective liquid membrane electrodes, based on the neutral carrier ETH 1001, inserted into an extracorporeal shunt established by means of indwelling catheters between the femoral artery and the femoral vein.

The blood is pumped from the artery to the vein, through the system containing the $Ca^{2+}$-selective electrodes, at a flow rate of 18 ml/h. A second peristaltic pump transports a reference electrolyte solution at a rate of 0.9 ml/h past a first, reference electrode to a second electrode, known as the common electrode, where it meets and mixes with the circulating blood. The mixed fluids are then returned to the animal's circulatory system.

The concentration of ionized calcium in the blood is measured potentiometrically as follows: The difference in potential between the reference electrode and the $Ca^{2+}$-selective electrode is measured differentially relative to the common electrode. The difference is amplified and the analogue signal produced by the amplifier is processed by a digital voltmeter and continuously recorded as a function of time, the difference in voltage being proportional to the $Ca^{2+}$ concentration.

The ionized calcium concentration in blood (1.1–1.2 mmol/liter) is about $10^5$ higher than the detection limit of the electrodes in aqueous solutions of calcium ($10^{-5}-10^{-6}$ mmol/liter). The method is capable of detecting a change of 0.003 mmol/liter or 0.3% in the $Ca^{++}$ concentration.

The anti-atherogenic activity has been confirmed also by measurement of the inhibition of neointimal lesion development in the rat carotid artery (balloon catheterization test, essentially as published in A. W. Clowes et al., Lab. Invest. 49 [1983]208–215).

In a first experiment a group of 12 rats was given PN 250 μg/kg/day in 10% ethanol-water s.c. A control group of 9 animals was non-injected and a further control group of 7 animals was vehicle-injected. Animals were randomized into 3 groups for catheterization and were weighed every other day throughout the study. Rats were anesthetized with ether inhalation. The thoracic region was shaved and the external branch of the left common carotid artery was isolated by an incision from the lower mandible to the clavicle, followed by retracting the submaxillary gland (lateral) and several muscle bundles including the sternohyoideus (medial), sternomastoideus (lateral) and digastricus posterior belly (lateral). The external carotid was carefully separated from surrounding tissue and guy sutures were placed distal to the superior thyroid artery (cephalad end ligated) and proximal (end open) to the heart for retraction. Lidocaine was applied to vasodilate during catheter introduction. Following an incision with iris scissors, a Fogarty arterial embolectomy catheter (No. 2F) was inserted into the external branch of the carotid, passed into the aortic arch and slightly withdrawn to assure inflation of the catheter within the common carotid artery. The catheter was inflated using approximately 900 mmHg air pressure, drawn distally and deflated. This was repeated three times to assure complete de-endothelialization of the common carotid. The catheter was removed, the artery ligated and the incision closed. Under these conditions the carotid is completely de-endothelialized.

Animals were sacrificed 14 days after ballooning in the same sequence as the catheterization. Thirty minutes before fixation the animals were injected with a 2.25% Evan's Blue dye solution (1.5 mg/kg iv) to differentiate between the neointimal and re-endothelialized areas. Areas of the carotid that have endothelial regrowth exclude the dye and appear white. The remaining areas that lack endothelium are stained blue. Whole body (beating heart) perfusion fixations (90–110 mmHg) were then performed on anesthetized (sodium pentobarbital, 50.0 mg/kg ip) animals using 200 ml of 1% glutaraldehyde in 0.15M sodium cacodylate buffer (pH 7.4, 37° C., 410 mOsm) followed by 400 ml of 3% glutaraldehyde in 0.15M sodium cacodylate. The entry site of the fixative was a puncture in the left ventricle, with efflux collected by vacuum suction from the right atrium. The thoracic aorta flow was restricted to optimize carotid perfusion. Successful fixation was judged by upper body rigidity and an absence of blood from the large arteries.

In a second experiment the procedure as described above was followed, with groups consisting of non-injected controls (n=8), animals treated with PY (n=5) or PN (n=8). Animals received drug for 2 days before catheterization and to the conclusion of the study (14 days). PY and PN were given at 1.0 mg/kg in 10% EtOH-water s.c. All animals (controls and drug-treated) were randomized into 3 groups for catheterization.

After each experiment the fixed carotid was removed and cut into 3 segments (distal, central, proximal). Tissue processing of only the central segment included 18 hours in 3% buffered glutaraldehyde, buffer rinsing, dehydration in an ascending ethanol series and infiltration with Spurr's resin. The samples were embedded with cross-sectional orientation so that sectioning (0.5 μm) would include blue areas which have not re-endothelialized and show continued proliferative responses. A two-step polychromatic stain utilizing toluidine blue and 1.0% basic fuchsin rendered histological differentiation to nuclear, cytoplasmic and extracellular connective matrix components.

All light microscopic histology slides were randomized, encoded and evaluated utilizing a Zeiss standard microscope and the Videoplan computerized image analyzer. Vessel measurements included maximum lesion height. Image calibration and magnification checks were performed for every group of slides analyzed. Analysis of groups was done using parametric and nonparametric statistical methods.

PN and PY were tolerated at all doses used, with control and treated animals showing similar weight gains. Maximal lesion height (μm) are tabulated in Table 1. Non-injected and s.c. vehicle controls (Expt. 1) gave equivalent values and have been combined for statistical purposes.

TABLE 1

| MAXIMAL INTIMAL HEIGHT (μm) FROM CONTROLS AND TREATED ANIMALS | | | |
|---|---|---|---|
| | Dose (mg/kg) | Intima | p-Value |
| Expt. 1 | | | |
| Controls n = 16 | — | 84.9 ± 21.3 | — |
| PN n = 11 | 0.25 | 63.2 ± 19.9 | p = 0.006 |
| Expt. 2 | | | |
| Controls n = 8 | — | 72.4 ± 17.4 | — |
| PY n = 5 | 1.0 | 58.6 ± 18.1 | p = 0.097 |
| PN n = 8 | 1.0 | 38.9 ± 22.0 | p = 0.002 |

The p values refer to comparisons between control and treated groups. Analysis was performed using a one-tail Student t-test. Similar values were obtained using nonparametric statistical analyses. All other values are mean ±SD for number of animals indicated.

It can be seen from Table 1 that when given at 0.25 mg/kg/d PN inhibited lesion development by 26%

(Expt. 1). Increasing the dose to 1.0 mg/kg/d resulted in 46% inhibition, whereas PY inhibited 19% at a similar dose (Expt. 2). Vessel diameters (determined from cross-sections of perfusion fixed vessels) were comparable in all three experiments.

This effect appears to be independent of blood pressure lowering effects or platelet involvement.

The compounds of the invention are therefore useful in the treatment of conditions related directly or indirectly to ionized calcium levels in the blood, in particular in the treatment of hypercalcaemic disorders
Morbus Paget
osteoporosis
arteriosclerosis and in particular atherosclerosis (prevention or inhibition of plaque formation)
algoneurodystrophy and
acute pancreatitis.

Preferred is the use in the treatment of arteriosclerosis and in particular atherosclerosis.

An indicated daily dosage is in the range of from about 0.2 to about 350 mg, preferably 1 to 70 mg, especially 1 to 10 mg i.v., and from about 2 to 2000 mg per os or from about 1 to about 200 mg sublingually for interval therapy. Preferred for PY, PN and PK is a daily dosage of from about 0.2 mg to about 10 mg i.v., from about 2 to about 50 mg per os or from about 1 to about 50 mg sublingually. Especially for interval therapy the unit dosage may be administered in divided dosages e.g. 3 times a day containing from about 0.1 to about 150 mg i.v. or about 0.7 to about 700 mg per os or about 0.3 to about 70 mg sublingually of the compound admixed with a solid pharmaceutical carrier or diluent.

Additionally we have found that combinations of calcium antagonists, hereinafter referred to as "the compounds of the invention", e.g. calcium antagonists having a 1,4-dihydropyridine structure having an aryl or heterocyclic group attached to the 4 position, especially compounds of formula I, with calcitonins, have particularly advantageous properties.

We have found that coadministration of calcium antagonists with calcitonins produces especially advantageous results. Such calcitonins are of any natural or synthetic origin and include human calcitonin, fish calcitonin and their derivatives, e.g. Salmon calcitonin, eel calcitonin, its derivative 1,7-Asu-eel calcitonin, hereinafter referred to as Elcitonin, and porcine calcitonin. Salmon calcitonin, hereinafter SMC, is preferred. In standard hypocalcaemic tests it is found that the compounds of the invention affect beneficially the hypocalcemic effect of calcitonins, in particular provide a prolongation thereof. For example in the rabbit test mentioned above initially calcitonin is injected at a dose of 0.1 to 5 international units per animal kg weight about 30 minutes before the test starts. The compound of the invention is administered in accordance with the details given above. The hypocalcemic effect of the calcitonin is measured with regard to time. It is observed that the compounds of the invention prolong the effects of the calcitonin.

An indicated daily dose of calcitonin is in the range 50 to 100% that normally used for known uses, e.g. 5 to 100 micrograms. This may be conveniently administered in unit dosage forms containing 10 to 100 international units. The administration route is preferably parenteral, e.g. intramuscular, subcutaneous or intravenous. An alternative mode of administration is nasal administration. The compounds of the invention, and calcitonin, may be administered in any conventional manner used for standards in the same indications as mentioned above.

Results obtained in the rabbit test mentioned above with the preferred compounds PN and SMC are as follows:

| PN alone: | | |
|---|---|---|
| Posology | Dose | Lowering of ionized calcium[1] |
| Intravenous infusion | 0.5 mg/0.5/over 1 hour | 10–20% |
| Oral | 1 mg/kg | 5–10% |

[1] By calcium ion selective electrode

The intravenous experiment is repeated measuring total calcium photometrically. Drop in calcium levels over 1½ hours = 23%, over 2½ hours = 30%.

| SMC + PN (given at the same dosage as above 30 minutes after SMC): | |
|---|---|
| SMC dose: 1 international unit/kg intravenous | |
| PN posology | Prolongation of SMC hypercalcemic effect[1] |
| intravenous infusions | 2–5 hours |
| oral | 1–3 hours |

[1] By calcium ion selective electrode

PN may thus be administered to larger mammals at an oral dose of from 2 to 20 mg. SMC may be co-administered at about 70% of the normal dosage of the same duration for the same mode of administration.

The compounds of the invention and calcitonin may be administered in the same way as for other uses and in free form or in salt form as appropriate. The same formulations may be used.

In another aspect the present invention provides a pharmaceutical composition comprising a compound of the invention and a calcitonin. In a yet further aspect the invention provides a compound of the invention and a calcitonin in association therewith for use in the treatment of conditions related directly or indirectly to ionized calcium levels in the blood, in particular in the treatment of hypercalcaemic disorders
Morbus Paget
osteoporosis
arteriosclerosis and in particular atherosclerosis (prevention or inhibition of plaque formation)
algoneurodystrophy and
acute pancreatitis.

In a further aspect the invention provides a pack or dispenser device containing a pharmaceutical composition comprising a compound of the invention and additionally a pharmaceutical composition containing a calcitonin together with instructions for use in the indications mentioned above.

In a further aspect the invention provides the use of a compound of formula I in the manufacture of a pharmaceutical composition for the treatment of conditions related directly or indirectly to ionized calcium levels in the blood, in particular of conditions as mentioned above.

The compounds of the invention may be administered on their own or in the form of pharmaceutical compositions. Such compositions conveniently contain more than 1% by weight of the compound of the invention and may be prepared by conventional techniques to be in conventional forms, for example capsules, tablets, suppositories, dispersible powders, suspensions, for enteral or parenteral administration. Suitable pharmaceutical diluents or carriers include, for example, alcohols, e.g. polyethyleneglycol, polyvinylpyrrolidone, mannitol and lactose as well as suitable preserving agents, such as ethyl-p-hydroxybenzoate, suspending agents such as methyl cellulose, tragacanth and sodium alginate, wetting agents such lecithin, polyoxyethylene stearate and polyoxyethylene sorbitan mono-oleate, granulating and disintegrating agents such as starch and alginic acid, binding agents such as starch, gelating and acacia, and lubricating agents such as magnesium stearate, stearic acid and talc, in order to provide an elegant and palatable pharmaceutical preparation.

In view of the low solubility of many of the compounds of the invention it is preferred to employ solid forms. It is preferred to use pharmaceutical compositions formulated to facilitate rapid absorption of a compound of the invention. For example oral pharmaceutical compositions may be employed and formulated to dissolve rapidly in the mouth, e.g. sub-lingual tablets and capsules. Alternatively the pharmaceutical compositions may be in powder or liquid form for administration as a spray or mist into the oral cavity.

It is contemplated that a spray applicator, e.g. an atomizer, may be used for administering such a spray or mist. Such spray applicators are known, for example atomizers for administering a liquid spray, and powder blowers which may be constructed to receive a cartridge containing a unit dosage of a liquid or powder pharmaceutical composition, break the cartridge, and expel the contents in the form of a spray or mist. Alternatively a pressurized container may incorporate a pharmaceutical composition in the form of a powder or liquid and compressed gas for expelling the compositions.

Naturally metering devices may be incorporated to facilitate administration of a predetermined amount of the pharmaceutical composition.

Compositions containing calcitonins are well known. They may be e.g. liquid for nasal or perenteral administration. If desired the calcitonins may be combined with a compound of the invention in a appropriate form, e.g. in liquid form.

All these devices and the techniques used for formulating suitable pharmaceutical compositions are well known.

The pack or dispenser device may contain a plurality of unit dosage forms containing a compound of the invention. These may be packed in metal or plastic foil, e.g. as a blister pack. The pack or dispenser may be provided with instructions for administration of a compound of the invention in the treatment of the conditions mentioned above.

The following Examples are illustrative of compositions for use in the invention.

EXAMPLE 1

Hard gelatine capsules for oral administration

Hard gelatine capsules containing the ingredients indicated below may be prepared by conventional techniques, and be administered once a day for the treatment of conditions related directly or indirectly to ionized calcium levels in the blood:

| Ingredient | Weight |
| --- | --- |
| PN | 10.0 mg |
| Polyvinylpyrrolidone | 30.0 mg |
| Lactose | 148.5 mg |
| Corn starch | 60.0 mg |
| Magnesium stearate | 1.5 mg |
| | 250.0 mg |

EXAMPLE 2

Tablets for sublingual administration

| Ingredient | Weight |
| --- | --- |
| PN | 10.0 mg |
| Polyethyleneglycol 6000 | 33.0 mg |
| Mannitol | 50.0 mg |
| Polyvinylpyrrolidone | 4.5 mg |
| Talc | 2.0 mg |
| Magnesium stearate | 0.5 mg |
| | 100.0 mg |

EXAMPLE 3

Soft gelatine capsules for sublingual administration

| Ingredient | Weight |
| --- | --- |
| PN | 10.0 mg |
| Polyethyleneglycol 2000 | 100.0 mg |
| Polyethyleneglycol 400 | 140.0 mg |
| | 250.0 mg |

Sufficient amounts of the above components are mixed in conventional manner and filled into gelatine capsules or compressed to tablets, which are administered once a day for the treatment of conditions related directly or indirectly to ionized calcium levels in the blood.

EXAMPLE 4

Salmon calcitonin ampoules

Ampoules suitable for parenteral administration and containing the following sterile ingredients may be produced in conventional manner. The ampoules may be used with any of Examples 1 to 3, at a dose of 1 to 4 ampoules daily.

| Constituents | Weight | |
| --- | --- | --- |
| Synthetic salmon calcitonin (polyacetate, polyhydrate) | 0.0000725 | g [+)] |
| Glacial acetic acid | 0.0020 | g |
| Sodium acetate | 0.0020 | g |
| Sodium chloride | 0.00750 | g |
| Water for injection up to | 1.0040 | g |
| | 1.0 | ml |

[+)] corresponding to 0.000050 g of synthetic salmon calcitonin

EXAMPLE 5

Composition containing salmon calcitonin suitable for nasal administration

| Ingredient | Quantity (per ml) |
| --- | --- |
| 1) Salmon calcitonin (active ingredient) | 0.1375 mg |
| 10% excess | 0.01375 mg |

-continued

| Ingredient | Quantity (per ml) |
| --- | --- |
|  | 0.15125 mg |
| 2) NaCl | 7.5 mg |
| 3) Benzalkonium chloride | 0.1 mg |
| 4) HCl (1N) | added to ph 3.7 |
| 5) Distilled water | to an end volume of 1.0 ml |

Components 1) to 3) are combined under protection of nitrogen gas (on a scale to produce a final volume of 2500 ml) in conventional manner, with 10% of salmon calcitonin being added to allow for loss at filtration. 4) is then added to bring the pH to 3.7 and distilled water added to an end-volume of 2500 ml. The obtained solution is filtered (e.g. using a 0.2 μm filter) to give a composition suitable for nasal dispensor with a solution volume of 2 ml. The composition comprises ca. 550 MRC-units active ingredient/ml, and the applicator delivers a quantity comprising 55 units per actuation.

Example 5 is administered concomitantly with anyone of examples 1 to 3.

We claim:

1. A method for treating arteriosclerosis which comprises administering a therapeutically effective amount of 4-(2,1,3-benzoxadiazol-4-yl)-1,4-dihydro-2,6-dimethyl-3-methoxycarbonyl-pyridine-5-carboxylic acid isopropyl ester to a subject in need of such treatment.

2. A method for treating atherosclerosis which comprises administering a therapeutically effective amount of 4-(2,1,3-benzoxadiazol-4-yl)-1,4-dihydro-2,6-dimethyl-3-methoxycarbonyl-pyridine-5-carboxylic acid isopropyl ester to a subject in need of such treatment.

3. A method for preventing or inhibiting plaque formation which comprises administering a therapeutically effective amount of 4-(2,1,3-benzoxadiazol-4-yl)-1,4-dihydro-2,6-dimethyl-3-methoxycarbonyl-pyridine-5-carboxylic acid isopropyl ester to a subject in need of such treatment.

4. A method for treating arteriosclerosis which comprises administering a therapeutically effective amount of 4-(2,1,3-benzoxadiazol-4-yl)-1,4-dihydro-2,6-dimethylpyridine-3,5-dicarboxylic acid diethyl ester to a subject in need of such treatment.

5. A method for treating atherosclerosis which comprises administering a therapeutically effective amount of 4-(2,1,3-benzoxadiazol-4-yl)-1,4-dihydro-2,6-dimethyl-pyridine-3,5-dicarboxylic acid diethyl ester to a subject in need of such treatment.

6. A method for preventing or inhibiting plaque formation which comprises administering a therapeutically effective amount of 4-(2,1,3-benzoxadiazol-4-yl)-1,4-dihydro-2,6-dimethylpyridine-3,5-dicarboxylic acid diethyl ester to a subject in need of such treatment.

* * * * *